(12) United States Patent  
Wimmer

(10) Patent No.: US 9,522,044 B2  
(45) Date of Patent: Dec. 20, 2016

(54) TREATMENT CHAMBER FOR TREATING SURGICAL OR DENTAL INSTRUMENTS WITH ELECTRICAL ENERGY USING CHAMBER WALL MADE OF THIN FILM OR THICK FILM

(71) Applicant: W&H Dentalwerk Bürmoos GmbH, Bürmoos (AT)

(72) Inventor: Stefan Wimmer, Ostermiething (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 0 days.

(21) Appl. No.: 14/742,678

(22) Filed: Jun. 17, 2015

(65) Prior Publication Data

US 2015/0282884 A1 Oct. 8, 2015

Related U.S. Application Data

(63) Continuation of application No. PCT/EP2013/077271, filed on Dec. 19, 2013.

(30) Foreign Application Priority Data

Dec. 20, 2012 (EP) .................................. 12198313

(51) Int. Cl.
```
A61L 2/00      (2006.01)
B08B 3/00      (2006.01)
B08B 3/04      (2006.01)
A61B 19/00     (2006.01)
A61C 19/00     (2006.01)
A61L 2/07      (2006.01)
A61L 2/16      (2006.01)
```
(52) U.S. Cl.
CPC ............... *A61B 19/34* (2013.01); *A61B 90/70* (2016.02); *A61C 19/002* (2013.01); *A61L 2/07* (2013.01); *A61L 2/16* (2013.01); *A61C 2204/005* (2013.01)

(58) Field of Classification Search
CPC ......... A61B 90/70; A61C 19/002; A61L 2/07; A61L 2/16; A61C 2204/005
USPC .................. 422/295, 299; 134/94.1, 105–107
See application file for complete search history.

(56) References Cited

U.S. PATENT DOCUMENTS

| | | | |
|---|---|---|---|
| 5,840,248 A * | 11/1998 | Ongaro | ..................... A61L 2/07 237/40 |
| 2004/0001783 A1 | 1/2004 | Bowen | |
| 2004/0126274 A1 | 7/2004 | Song et al. | |
| 2008/0012291 A1 | 1/2008 | Helfenbein et al. | |
| 2011/0206555 A1 | 8/2011 | Wiek et al. | |

FOREIGN PATENT DOCUMENTS

| | | |
|---|---|---|
| DE | 202012002701 | 6/2012 |
| EP | 2246010 | 11/2010 |

* cited by examiner

*Primary Examiner* — Monzer R Chorbaji  
(74) *Attorney, Agent, or Firm* — Klarquist Sparkman, LLP

(57) ABSTRACT

A treatment chamber or treatment carrier for use in a device for treating a medical or dental instrument. The device comprises a housing, which at least partially surrounds the instrument. The device also comprises at least one conductor made of an electrically conductive material layer applied to the housing for converting electrical energy into thermal energy, and at least two electrical contacts embedded in the conductor for supplying the at least one conductor with electrical energy. A treatment device having such a treatment chamber and/or such a treatment carrier is also described.

32 Claims, 3 Drawing Sheets

TREATMENT CHAMBER FOR TREATING SURGICAL OR DENTAL INSTRUMENTS WITH ELECTRICAL ENERGY USING CHAMBER WALL MADE OF THIN FILM OR THICK FILM

CROSS REFERENCE TO RELATED APPLICATION

This is a Continuation of International Application No. PCT/EP2013/077271, filed Dec. 19, 2013, which was published in German under PCT Article 21(2), which in turn claims the benefit of pending European Patent Application No. 12198313.4, filed Dec. 20, 2012, which are incorporated herein by reference.

BACKGROUND

Field

This application relates to a treatment chamber or a treatment carrier for use in a device for treating at least one medical or dental instrument, as well as a treatment device having such a treatment chamber and/or such a treatment carrier.

Description of Prior Art

Treatment devices are used for cleaning, disinfecting, sterilizing and/or caring of medical, in particular dental, instruments. Instruments to be treated are understood in particular to include straight, curved or pistol-shaped handpieces as well as parts of handpieces, e.g., handpiece heads having a tool receptacle for receiving a treatment tool, adapters and couplings. Supply lines for driving the treatment tool as well as fluid lines often run through the handpieces. In particular, these lines are transmission channels or fluid channels for air, water or spray.

For treating the medical instruments, in particular their drive channels as well as fluid channels, the devices, in particular the sterilizers, autoclaves or thermal disinfectors introduce at least one operating medium into a treatment chamber in which the at least one medical, in particular dental, instrument is carried, preferably by means of a treatment carrier, or they feed the medium directly to the at least one medical instrument. Liquids, for example, hot water or steam, in particular saturated steam, are preferably used as the operating media.

It is known in the state of the art that the operating media are heated to a treatment temperature in the treatment devices. To do so, heating devices are provided in the treatment devices. In sterilizers and autoclaves these devices are designed as independent vaporizers, which convert water as an operating medium into saturated steam. The steam is then sent through at least one line to the treatment chamber, the treatment carrier or directly to the medical instrument to heat the medical instrument to 134 degrees Celsius.

Furthermore, it is known in the state of the art, in particular in the case of sterilizers and autoclaves, that the treatment chambers of the treatment devices can be preheated by means of additional heating elements, which are also provided in the treatment devices. This makes it possible to reduce the amount of steam needed to heat the at least one medical instrument to 134 degrees Celsius. The heating elements here are arranged in the treatment devices in such a way that they are in thermal contact with the treatment chambers, so that there is a transfer of heat from the heating elements to the treatment chambers.

One disadvantage of these embodiments of the treatment devices has proven to be the arrangement of the plurality of heating devices and/or heating elements, in particular as independent units, in the treatment devices.

Due to the design of the heating devices and/or the heating elements as independent components, it is necessary to transfer the quantities of heat generated from the heating devices and/or heating elements directly or indirectly by means of one or more operating media to the treatment chambers, treatment carriers or medical instruments. However, this transfer of the quantities of heat generated is associated with disadvantages. In particular, the transmission of the operating media from the heating devices to the treatment chambers by means of fluid lines or media lines results in thermal losses. In addition, the coupling of the independent heating elements to the treatment chambers constitutes a problem. To minimize the thermal losses in the transfer of the thermal energies, it is necessary to adapt the heating elements to the shapes of the treatment chambers. However, the chambers themselves are preferably adapted to the shape of the medical instruments to be treated and therefore have complex shapes in some cases, which makes the coupling of the heating elements to the treatment chambers difficult.

Another disadvantage is the need for space in the treatment devices for the plurality of heating devices and/or heating elements as well as their connecting lines to the treatment chambers. These heating devices must be accommodated in the treatment devices in addition to the treatment chambers, the control units as well as additional relevant components. This in turn interferes with a user-friendly design of the treatment devices, in particular with a space-saving design of the devices.

Other disadvantage is the high cost of the numerous components, in particular for heating the operating media, for thermally insulated transport of the media and for preheating the treatment chambers.

SUMMARY

Therefore, one object of the present invention is to create a treatment chamber or a treatment carrier, as well as a device for treating at least one medical or dental instrument with such a treatment chamber or such a treatment carrier, such that it will be simple to produce while also avoiding the disadvantages of the prior art and in particular making it possible to generate thermal energy in the treatment device in a space-saving manner and transfer it to the at least one medical instrument that is to be treated as well as to prevent thermal losses in the treatment device.

To solve this problem, according to a first exemplary embodiment, a treatment chamber or a treatment carrier is proposed for use in a device for treating of at least one medical or dental instrument, having a housing, which at least partially surrounds the at least one medical instrument, wherein the housing has at least one conductor made of an electrically conductive material for converting electrical energy into thermal energy and has at least two electric contacts for supplying the at least one conductor with electrical energy.

According to a second exemplary embodiment, the at least one conductor has a carrier layer and/or a cover layer of a dielectric material to electrically insulate the conductor. In particular when using the treatment chamber or the treatment carrier in a device for sterilization of the medical instruments, the treatment chamber and/or the carrier is manufactured from an electrically conductive material, in particular stainless steel. To position the at least one conductor directly on the chamber, in particular on its inside or outside, or electrically insulated on the carrier, a carrier layer is applied to the chamber or to the carrier according to the invention. The cover layer, which also comprises a dielectric material serves to electrically insulate the at least one conductor with respect to the at least one medical instrument to be treated and/or additional components, in particular those that are electrically conductive, in the treatment device, which in particular are positioned in proximity to the treatment chamber or the carrier.

The at least one conductor made of an electrically conductive material for converting electrical energy into thermal energy as well as the carrier layer and the cover layer are preferably each formed by a thin film or a thick film. These layers are preferably applied directly to the treatment chamber or to the treatment carrier by a coating method, in particular by a thin-film or a thick-film method.

Thus the treatment chamber or the treatment carrier is characterized by a conductor applied directly to the treatment chamber or the carrier and formed by a coating, in particular by a thin film or a thick film. Furthermore, the carrier layer and/or the cover layer are formed by a coating, in particular by a thin film or a thick film.

According to another exemplary embodiment, the at least one conductor has a plurality of sections, which are arranged at different distances from one another on the housing of the treatment chamber or the treatment carrier. It is possible in this way to vary the amount of heat generated per area unit on the housing, so that a homogeneous temperature distribution can be achieved in the chamber or the carrier. The housing of the treatment chamber or the carrier having the at least one conductor is preferably divided into two subareas, wherein a first subarea is situated beneath a second subarea, as seen vertically. To create a homogeneous temperature distribution in the chamber, the plurality of sections of the at least one conductor have smaller spacings in the lower subarea than in the upper subarea.

According to another exemplary embodiment, the at least one conductor is arranged on the housing of the treatment chamber or the treatment carrier in such a way that it surrounds the at least one medical instrument on at least two sides. The conductor here preferably extends in the form of a coil around the at least one medical instrument and along its longitudinal axis, in particular in the axial and radial directions. In addition, a second conductor, in particular one in a spiral shape or a helical shape, is preferably arranged on another side of the housing. This can preferably be supplied with electrical energy separately and can thus be controlled.

According to another exemplary embodiment, the at least two conductors are arranged on the housing in such a way that at least one of the two conductors is arranged between the other conductor, respectively. The conductors thus mesh with one another.

According to one additional exemplary embodiment, the housing of the treatment chamber or the treatment carrier has at least one media feed for introducing at least one operating medium into the treatment chamber or into the treatment carrier. This is preferably designed as a nozzle. The operating medium supplied is preferably directed at the second conductor, which is designed in particular as a spiral, to heat the medium directly in the chamber or the carrier. The second conductor thus additionally serves as a heating element for heating and/or evaporating the operating medium. In addition to the media feed, the treatment chamber or the treatment carrier preferably has at least one media outlet to carry the operating medium out of the chamber or the carrier.

According to another exemplary embodiment, the housing of the treatment chamber or the treatment carrier has at least one connecting device for receiving the at least one medical instrument. The connecting device itself may also be designed as a media feed at the same time. It preferably comprises a connecting coupling for connecting the at least one medical instrument, in particular a handpiece or an angle piece.

According to an additional exemplary embodiment, the housing of the treatment chamber or of the treatment carrier is formed by at least one first and one second housing part, which are connected to one another, so that they are rotatable or displaceable in relation to one another, for introducing and removing the at least one medical, in particular dental, instrument. The housing here preferably has two conductors for converting electrical energy into thermal energy, wherein a first conductor is arranged on the first housing part and a second conductor is arranged on the second housing part.

According to a first exemplary embodiment of the device for treating at least one medical, in particular dental, instrument, it comprises a control unit for controlling and/or regulating a treatment process, a power supply for connecting the treatment device, in particular the control unit, to an energy source, at least one media supply having at least one media storage device and/or at least one connection for an external media source as well as a treatment chamber and/or a treatment carrier for the at least one medical, in particular dental, instrument, wherein the treatment chamber and/or the treatment carrier is designed according to any one of the exemplary embodiments described above.

According to a second exemplary embodiment of the device for treating at least one medical, in particular dental, instrument, the treatment device has a door, wherein the control unit, the power supply or the media supply and at least one of the two housing parts of the treatment chamber or of the treatment carrier is/are arranged in or on the door of the treatment chamber. Due to this arrangement of the components required for the treatment process as well as the at least one conductor in or on the door of the treatment device, it is possible to design it as a standard component and to use it for treatment devices of various designs. In particular, these treatment devices differ with regard to the size of the treatment space.

According to another exemplary embodiment of the treatment device, the control unit has a circuit for identification of the at least one instrument accommodated in the treatment chamber or in the treatment carrier. To do so, the at least one conductor, preferably in the form of a coil for converting electrical energy into thermal energy, which is arranged on the housing of the treatment chamber or of the treatment carrier, is connected to the control unit and is designed for sending and/or receiving data and/or energy. Data and/or energy may thus be transmitted between the instrument, in particular between a memory unit in or on the medical instrument, and the treatment device in order to automatically select the treatment process for the medical instrument based on the data transmitted.

According to another exemplary embodiment of the treatment device, the control unit has a circuit for generating eddy currents in the treatment chamber or in the treatment carrier. The at least one conductor is therefore designed for converting electrical energy into thermal energy on the housing of the treatment chamber or on the treatment carrier for generating alternating magnetic fields.

The present treatment chamber, the treatment carrier and the treatment device are characterized by a number of substantial advantages.

One advantage of the present invention is the possibility of generating the required thermal energy directly on and/or through the treatment chamber or the treatment carrier itself. It is no longer necessary to transfer the quantities of heat thereby generated from a separate and independent heating device and/or heating element to the treatment chamber. This eliminates the thermal losses associated with such a transfer.

Another advantage of the invention is the possibility of designing the treatment chamber or the treatment carrier independently of the heating element. Due to the arrangement of the conductor for converting electrical energy into thermal energy directly on the chamber or the carrier, it is possible to design the shape of the housing in any desired manner, in particular to adapt it to the shape of the medical instrument to be treated.

In addition, designing the at least one conductor using a coating method, in particular a thin-film or a thick-film method, constitutes an advantage. The design of the at least one conductor as a thin film or a thick film makes it possible to heat the conductor, in particular the treatment chamber or the treatment carrier rapidly, because of the small mass of the layer.

The possibility of a user-friendly design of the treatment devices constitutes another advantage of the invention. Due to the design of the treatment chamber or the treatment carrier with a conductor made of an electrically conductive material for converting electrical energy into thermal energy, it is possible to generate the thermal energy directly on the treatment chamber. Heating equipment and/or heating elements and connecting lines installed separately are no longer needed. This permits optimization of the construction size of the treatment device, in particular its housing.

The mounting of an additional conductor, a second or third conductor, in particular a replacement conductor, which is put into operation only when there is a defect in the first or second conductor, additionally permits a simple and easy repair of a defective heating element of the treatment device.

BRIEF DESCRIPTION OF THE DRAWINGS

The invention is explained in greater detail below on the basis of a plurality of exemplary embodiments and in conjunction with the accompanying drawings, in which.

DETAILED DESCRIPTION

Figure 1:
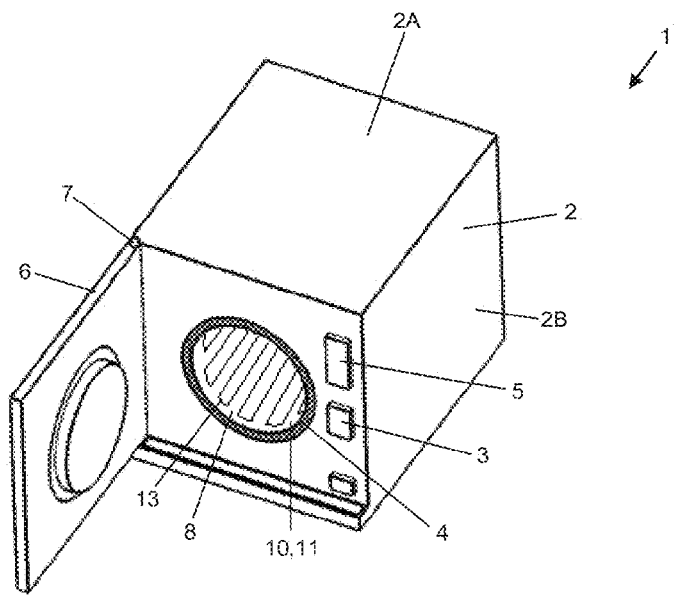
FIG. 1 shows a perspective diagram of a first exemplary embodiment of a treatment device for treating at least one medical, in particular dental, instrument.

FIG. 1 shows a first exemplary embodiment of a treatment device 1 for treating at least one medical, in particular dental, instrument. It is preferably designed in the form of a sterilizer 1, in particular a steam sterilizer. The sterilizer 1 comprises a housing 2 having a plurality of exterior walls 2A, 2B. An exterior wall, in particular a side wall, preferably forms the operating side of the cleaning or care device 1. It has a plurality of operating elements 3, which preferably serve to select various operating programs or to set operating parameters. A display screen 5 displays the selected operating programs or parameters of the selected treatment process. In addition to the operating elements 3, the housing 2 of the sterilizer 1 has an opening 4 that is connected to a treatment chamber 8 of the sterilizer 1. An instrument to be treated or a treatment carrier for the at least one medical instrument can be introduced into or removed from the treatment chamber 8 through the opening 4. The opening 4 can be closed by means of a door 6, which is preferably mounted so it can rotate about a hinge 7 in relation to the plurality of walls 2A, 2B of the sterilizer 1.

The treatment chamber 8 itself is formed by a housing 10, which is preferably made of stainless steel. At least one part of the housing 10 is preferably arranged on the door 6, which is mounted to be rotatable or slidable in relation to the housing 10 for introducing and removing the at least one medical, in particular dental, instrument. At least one first conductor 13 made of an electrically conductive material for converting electrical energy into thermal energy is arranged on the inside 11 of the housing 10. It is possible in this way to generate thermal energy directly on and/or through the treatment chamber 8. Alternatively, the conductor 13 may also be mounted on the outside of the housing 10. To position the at least one conductor 13 directly on the chamber 8, in particular on the electrically conducting chamber housing 10, so that it is electrically insulated, the conductor 13 has a carrier layer and/or a cover layer made of a dielectric material. Both the conductor 13 and the plurality of layers are preferably formed by a thin-film technique or a thick-film technique.

In this exemplary embodiment, the at least one conductor 13 is arranged on the housing 10 of the treatment chamber 8 in such a way that it surrounds the treatment chamber 8 on at least two sides. The conductor therefore extends preferably in a coil on the housing 10 of the chamber 8. Alternatively, the conductor 13 may be designed in the form of a helix, which is coiled around the treatment chamber 8, preferably being designed in the form of a cylinder, in particular around its lateral surface.

The treatment chamber 8 itself is preferably designed to be detachable from the sterilizer 1.

Figure 2:
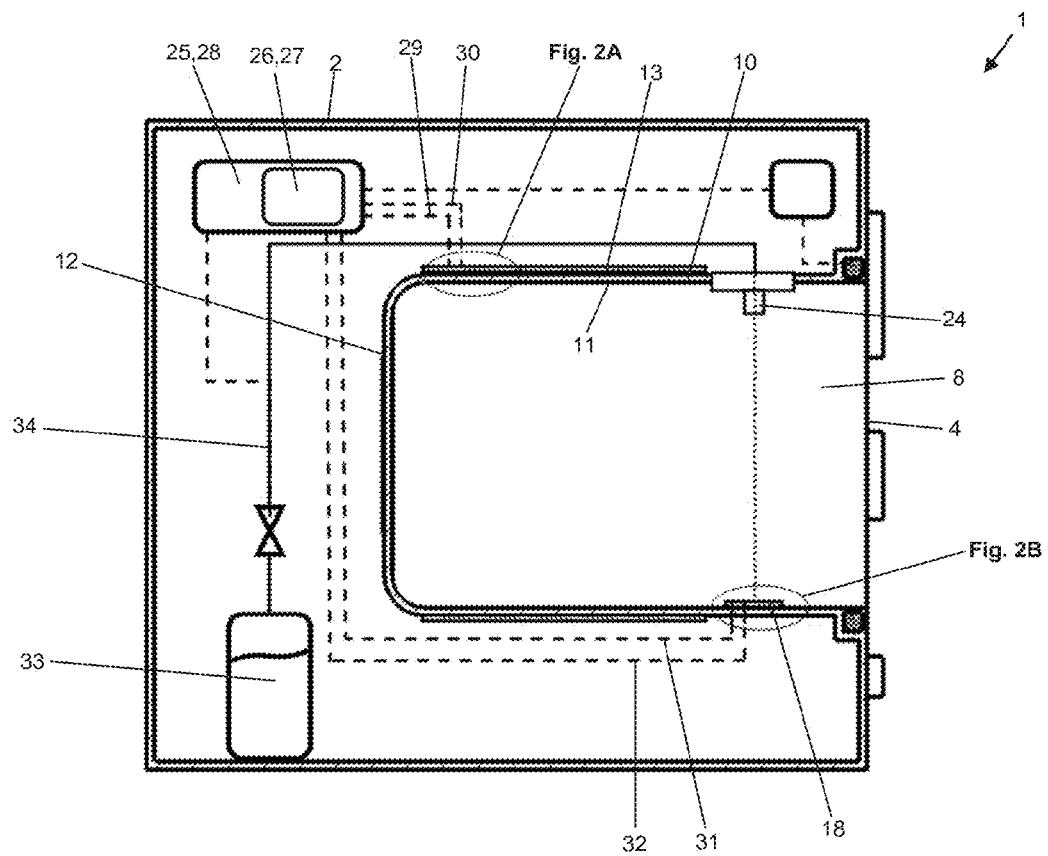
FIG. 2 shows a schematic diagram of a section through the treatment device from FIG. 1, FIG. 2A also shows a sectional diagram of a detail of the housing of the treatment chamber from FIG. 2, FIG. 2B also shows a sectional diagram of another detail from the housing of the treatment chamber from FIG. 2.

FIG. 2 shows in a sectional diagram the first exemplary embodiment of the treatment device 1 from FIG. 1 in a schematic diagram. In the interior of the housing 2 of the sterilizer 1, at least one control unit 25 as well as additional components, such as a power supply 28 for connecting to the sterilizer 1, in particular the control unit 25, to an energy source and a media supply 33, that are required for the treatment process are provided in addition to the treatment chamber 8, which is accessible through the opening 4. The treatment chamber 8 of the sterilizer is preferably designed as a pressurized vessel.

The media supply 33 comprises at least one media storage device for a working medium or a media connection for connecting the sterilizer 1 to an external media source. In addition, the media supply 33 has means for conveying the at least one treatment medium into the treatment chamber 8 in particular, such as valves, pumps or media lines 34, for example. The media lines 34 are therefore preferably connected to the treatment chamber 8, in particular by at least one media feed 24, which is preferably designed as a nozzle. In addition, the treatment chamber 8 has at least one media outlet for draining the media conducted into the chamber.

The control unit 25 preferably comprises at least one control circuit, a microcontroller and sensors, in particular at least one temperature sensor in the treatment chamber 8 for detection of operating parameters. In addition, the control unit 25 is connected by control lines to the media supply 33, to the operating elements and to the display. For at least one first conductor 13 and one second conductor 18, the sterilizer 1 has at least two electrical supply lines 29, 30 and 31, 32, which connect the conductors 13 and 18 electrically to the control unit 25 and/or the power supply 28. The control unit 25 thereby controls and/or regulates the operation of the treatment device 1.

According to a second exemplary embodiment of the treatment chamber 8, as shown in FIG. 2, the housing 10 of the treatment chamber 8 has a first conductor 13 on the outside 12 of the housing 10 and a second conductor 18 on the inside 11. The two conductors 13, 18 can preferably be supplied with electric power separately over lines 29, 30 and 31, 32. In particular, the first conductor 13 serves to preheat the treatment chamber 8. The second conductor 18 preferably serves to heat and/or evaporate the operating medium. To this end, the operating medium is guided by means of the media supply 24 directly onto the second conductor 18, which is designed in particular in the form of a spiral to heat and/or evaporate the medium directly in the chamber 8.

The control unit 25 preferably also has a circuit 26 for identification of the at least one instrument accommodated in the treatment chamber 8 or in the treatment carrier 9. The at least one conductor 13 or 18 is therefore formed on the housing 10 of the treatment chamber 8 for sending and/or receiving data and/or energy. This is preferably in the form of a coil. Data and/or energy may thus be transferred between the instrument, in particular between a memory/storage unit in or on the medical instrument and the treatment device 1. The circuit 26 is preferably designed to monitor the treatment process performed by the sterilizer 1 and to transmit data about the process by means of the at least one conductor 13 or 18 to the at least one medical instrument when the sterilizer 1 has actually completed the treatment.

In addition, the control unit 25 preferably has a circuit 27 for generating eddy currents in the treatment chamber 8. The at least one conductor 13 or 18 on the housing 10 of the treatment chamber 8 is therefore designed for generating alternating magnetic fields. Energy is thereby preferably transmitted in the form of an alternating electromagnetic field to the medical, in particular metallic, instruments, where it is converted into heat.

According to an alternative exemplary embodiment, the components of the sterilizer 2 shown in FIG. 2, in particular the control unit 25, the power supply 28, the media supply 33 and the media feed 24 may be provided in the door 6 of the sterilizer 1. Together with a part of the housing 10 of the treatment chamber 8, which has the at least one first conductor 13, the door thus forms a modular component that makes it possible to use it for a plurality of treatment devices having various designs.

Figure 2A:
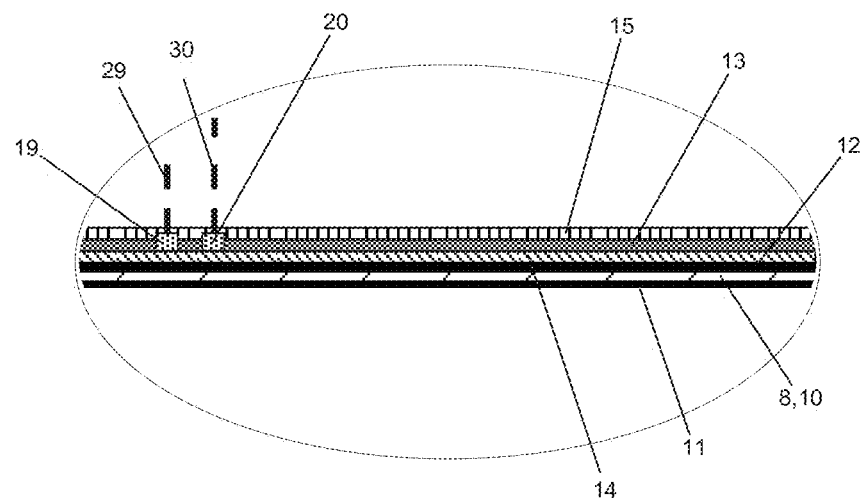

FIG. 2A shows a first detail of the housing 10 of the treatment chamber 8 from FIG. 2. To position the at least one conductor 13 directly on the chamber 8, in particular on its outside 12, so that it is electrically insulated, a carrier layer 14 made of a dielectric material is applied to the chamber 8 according to the invention. The cover layer 15, which also comprises a dielectric material, serves to insulate the at least one conductor 13 electrically with respect to electrically conductive components in the treatment device 1, which are arranged in proximity to the treatment chamber 8 in the device 1.

The at least two electrical contracts 19 and 20, which serve to supply electricity to the at least one conductor 13, are preferably positioned on the carrier layer 14 or directly on the conductor 13 and are electrically connected thereto. For electrical insulation of the contacts 19 and 20, they are preferably also surrounded and/or coated by the cover layer 15. The electric feed lines 29 and 30, which are sheathed by a separate insulation, extend through the cover layer 15 to the electrical contacts 19 and 20.

Due to this arrangement of the conductor 13 directly on the chamber 8, it is possible to create thermal energy directly on the treatment chamber 8, in particular on its exterior side 12. The heat thereby generated diffuses through the housing 10 and radiates from the inside 11 of the housing 10 into the chamber 8.

Figure 2B:
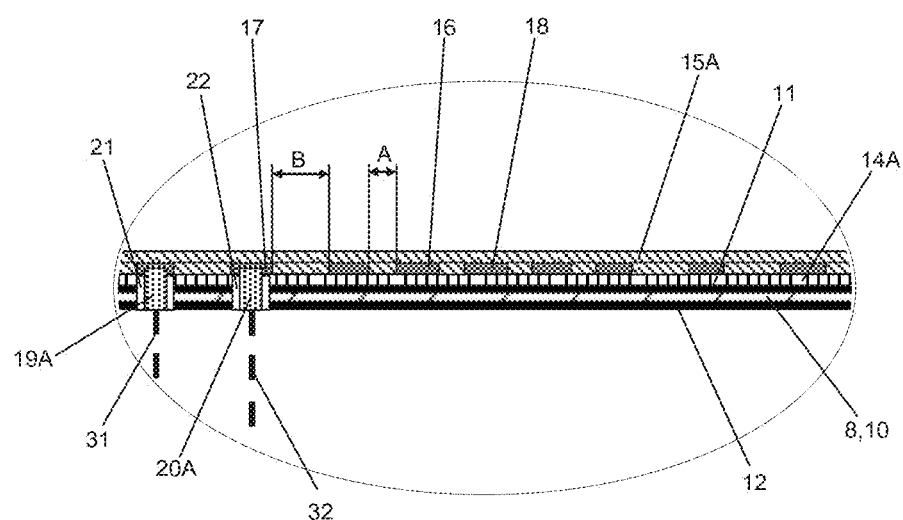

FIG. 2B shows a second detail of the housing 10 of the treatment chamber 8 from FIG. 2. The second conductor 18 is arranged on the inside 11 of the housing 10 of the treatment chamber 8 and is preferably designed in the form of a spiral for heating and/or evaporation of an operating medium. FIG. 2B in particular shows a section through the spiral-shaped conductor 18 and thus shows a plurality of sections 16, 17 of the conductor 18. These sections 16, 17 are preferably arranged at different distances A and B from one another. Thus, in this exemplary embodiment, the conductor 18 has smaller distances A between the sections 16 and 17 of the conductor 18 in a central region of the spiral than in an outer region of the conductor 18. The distance B between the distances 16, 17 in the outer circumference of the spiral is therefore greater. It is possible in this way to vary the amount of heat generated per area unit to the housing 10.

Again in this exemplary embodiment, the conductor 18 is arranged on a carrier layer 14A in order to position the conductor 18 on the inside 11 of the housing 10 in such a way that it is electrically insulated. To electrically insulate the conductor 18 with respect to the at least one medical instrument to be treated, the conductor is also covered with a cover layer 15A. This layer 15A preferably surrounds the conductor 18, in particular the plurality of sections 16, 17, on three sides, in particular on their top sides and/or on their lateral faces.

To supply electricity to the conductors 18 by means of electrical feed lines 31 and 32, the latter have at least two electrical contacts 19A and 20A. These are also preferably positioned on the carrier layer 14A, or they may also be positioned directly on the conductor 18 and remain electrically connected thereto. The conductor 18 is preferably contacted from the outside 12 of the housing 10 of the chamber 8. The contacts 19A and 20A therefore extend through the housing 10. To insulate the contacts 19A and 20A with respect to the electrically conductive housing 10, the contacts 19A and 20A are each surrounded by insulation 21 and 22. The insulation 21 and 22 is preferably designed to be cylindrical and has a central hole to receive the contacts 19A and 20A.

Figure 3:
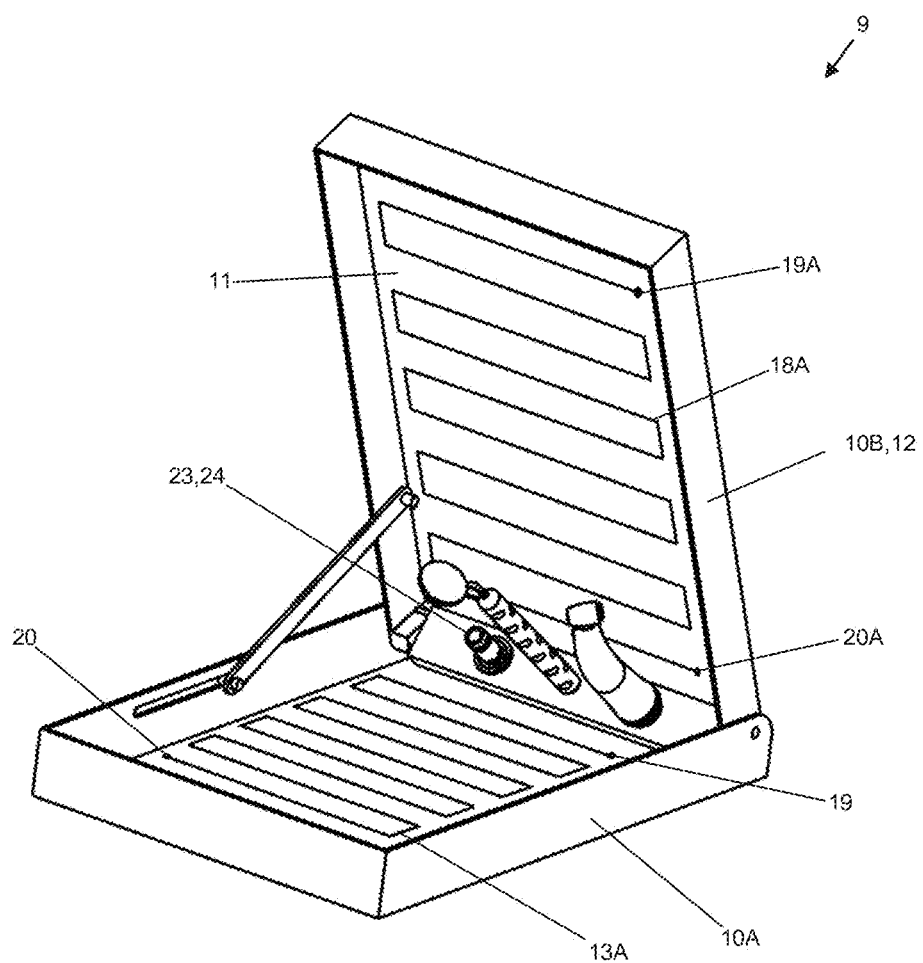
FIG. 3 shows a perspective diagram of a treatment carrier for accommodating at least one medical, in particular dental, instrument in a treatment device.

FIG. 3 shows a perspective diagram of a treatment carrier 9 for holding at least one medical, in particular dental, instrument in a treatment device 1. The treatment device 1 here is preferably designed for cleaning of the medical instruments by means of a fluid, for sterilization by means of saturated steam and for care by means of at least one lubricant. The treatment carrier 9 itself is formed by a first housing part 10A and a second housing part 10B, which are connected to one another so that they are movable relative to one another for introducing and removing the at least one medical, in particular dental, instrument. A plurality of connecting devices 23 are preferably arranged between the two housing parts 10A and 10B to receive the medical instruments to be treated. The connecting devices 23 therefore each have a common base, which in this exemplary embodiment is preferably mounted so it can rotate. The base here forms a third housing part, in particular the back side of the treatment carrier 9. The connection devices 23 in this exemplary embodiment are at the same time designed as a media feed 24. These connecting devices therefore have at least one hole, which connects the source of a treatment medium to the interior of the attached instruments, passing through them. Multiple holes are preferably provided in the connections 23, so that the instruments can be treated using a plurality of media. The holes preferably extend through the common base of the connections 23. If the treatment carrier 9 is inserted into a treatment device 1, then the holes are connected to the sources of the media via a coupling device. The housing 10A or 10B preferably has at least one additional media feed for introducing at least one operating medium into the treatment carrier 9, which is designed in particular in the form of one or more nozzles. These nozzles preferably serve to clean the exterior of the medical instruments.

According the invention, the housing parts 10A and 10B of the treatment carrier 9 additionally have at least one conductor 13A and 18A made of an electrically conductive material for converting electrical energy into thermal energy. The conductors 13A and 18A here are preferably arranged on the inside 11 of the two housing parts 10A, 10B and are preferably designed in the form of steps. To supply electrical energy to both conductors 13A and 18A, each comprises at least two electrical contacts 19, 20 and 19A, 20A. Through separate contacting of these two conductors 13A and 13B, they are each supplied with electrical energy separately. The conductors 13A and 13B, in particular the electric contacts 19, 20 and 19A, 20A are preferably contacted from the outside 12 of the housing parts 10A and 10B. The contacts 19, 20 and 19A, 20A therefore preferably extend through the housing parts 10A and 10B. If the housing parts 10A and 10B are manufactured from an electrically conductive material, the contacts 19, 20 and 19A, 20A are surrounded by insulation 21, 22 as already shown in FIG. 2B.

In addition, the conductors 13A and 18A each have a plurality of sections which are arranged at different distances from one another on the housing 10A, 10B of the treatment carrier 9. This, as well as the separate supply of electrical energy to the conductors 13A and 18A, makes it possible to vary the quantity of heat generated per area unit on the housing 10A, 10B, so that a homogeneous temperature distribution can be achieved in the carrier 9. The plurality of sections of the conductor 13A therefore has smaller spacings in the lower housing half 10A than the conductor 18A has in the upper half 10B.

In this exemplary embodiment of the treatment carrier 9, the conductors 13A and 18A also have a carrier layer and/or cover layer of a dielectric material to electrically insulate the conductors 13A and 18A. In this exemplary embodiment, the cover layer and backing layer as well as the electric conductors 13A and 13B are also embodied as a thin film or as a thick film.

The invention is not limited to the exemplary embodiment described here but instead includes all the embodiments that apply or include the basic logical function principal of the invention. In addition, all the features of all the exemplary embodiments described and presented here may be combined with one another. The conductors 13, 13A, 18 and 18A according to FIGS. 1 to 3 in particular are designed for sending and/or receiving data and/or energy and/or for generating alternating magnetic fields.

What is claimed is:

1. A treatment chamber or treatment carrier for use in a device for treating a medical or dental instrument, comprising:
    a housing which at least partially surrounds the instrument,
    at least one conductor made of an electrically conductive material layer applied to a surface of the housing for converting electrical energy into thermal energy, and
    at least two electrical contacts connected to the at least one conductor to supply electrical energy to the at least one conductor, and
    a dielectric carrier layer positioned on an inside of the housing, the at least one conductor positioned on the dielectric carrier layer and a dielectric cover layer positioned on the at least one conductor.

2. The treatment chamber or treatment carrier according to claim 1, wherein the at least one conductor comprises a plurality of sections, which are arranged on the housing at different distances from one another.

3. The treatment chamber or treatment carrier according to claim 1, wherein the at least one conductor is a first conductor, further comprising at least a second conductor which is arranged on at least one of an inside and an outside of the housing.

4. The treatment chamber or treatment carrier according to claim 3, comprising a second dielectric carrier layer, the at least one second conductor positioned on the second dielectric carrier layer and a second dielectric cover layer positioned on the at least one second conductor.

5. The treatment chamber or treatment carrier according to claim 1, wherein the at least one conductor is arranged on the housing to surround the at least one medical or dental instrument on at least two sides.

6. The treatment chamber or treatment carrier according to claim 1, wherein the at least one conductor is a first conductor, further comprising at least a second conductor, and wherein the first conductor and the second conductor can be separately supplied with electrical energy.

7. The treatment chamber or treatment carrier according to claim 1, wherein at least one of the at least one conductor, the dielectric carrier layer and the dielectric cover layer is formed by a thick-film or a thin-film coating.

8. The treatment chamber or treatment carrier according to claim 1, wherein the housing comprises at least one first housing part and at least one second housing part, which are connected so that the first and second housing parts can be rotated or displaced relative to one another for introducing and removing the instrument.

9. The treatment chamber or treatment carrier according to claim 1, wherein the housing comprises at least one connecting device for receiving the instrument.

10. The treatment chamber or treatment carrier according to claim 1, wherein the housing comprises at least one media feed for introducing at least one operating medium into the treatment chamber or into the treatment carrier.

11. A device for treating a medical or dental instrument, comprising:
    a control unit for controlling and/or regulating a treatment process,
    a power supply for connecting the treatment device to a power source,
    at least one media supply having at least one of a media storage device and a connection for an external media source, and a treatment chamber or a treatment carrier for the medical or dental instrument according to claim 1.

12. A device for treating a medical or dental instrument, comprising:
- a control unit for controlling and/or regulating a treatment process,
- a power supply for connecting the treatment device to a power source,
- at least one media supply having at least one of a media storage device and a connection for an external media source,
- a treatment chamber or a treatment carrier for the instrument, the treatment chamber or treatment carrier comprising a housing that at least partially surrounds the instrument and at least one conductor with a dielectric layer applied to an inner or outer side of the housing, wherein the treatment chamber or the treatment carrier is designed to be detachable from the treatment device.

13. The treatment device according to claim 12, wherein the control unit comprises a circuit for generating eddy currents in the treatment chamber or in the treatment carrier, and the at least one conductor is formed on the housing of the treatment chamber or on the treatment carrier for generating alternating magnetic fields.

14. A treatment chamber or treatment carrier for use in a device for treating a medical or dental instrument, comprising:
- a housing which at least partially surrounds the medical or dental instrument,
- at least one conductor made of an electrically conductive material layer applied to a surface of the housing for converting electrical energy into thermal energy, and
- at least two electrical contacts connected to the conductor to supply electrical energy to the at east one conductor, wherein
- the at least one conductor is arranged on the housing to surround the at least one medical or dental instrument on at least two sides.

15. The treatment chamber or treatment carrier according to claim 14, further comprising at least one of a dielectric carrier layer and a dielectric cover layer to electrically insulate the at least one conductor.

16. The treatment chamber or treatment carrier according to claim 15, wherein the dielectric carrier layer is arranged on one of an inside or outside of the housing, the at least one conductor is arranged on the dielectric carrier layer and the dielectric cover layer is arranged on the at least one conductor.

17. The treatment chamber or treatment carrier according to claim 15, wherein at least one of the dielectric carrier layer and the dielectric cover layer is formed by a thick-film or a thin-film coating.

18. The treatment chamber or treatment carrier according to claim 14, wherein the at least one conductor is formed by a thick-film or a thin-film coating.

19. The treatment chamber or treatment carrier according to claim 14, wherein the at least one conductor is arranged on at least one of an inside and an outside of the housing.

20. The treatment chamber or treatment carrier according to claim 14, wherein the at least one conductor is a first conductor, further comprising at least a second conductor, and wherein the first conductor and the second conductor can be separately supplied with electrical energy.

21. The treatment chamber or treatment carrier according to claim 14, wherein the housing comprises at least one of: a connecting device for connecting the instrument to the treatment chamber or treatment carrier and a media feed for introducing at least one operating medium into the treatment chamber or into the treatment carrier.

22. A device for treating a medical or dental instrument, comprising:
- a control unit for controlling and/or regulating a treatment process,
- a power supply for connecting the treatment device to a power source,
- at least one media supply having at least one of a media storage device and a connection for an external media source, and
- a treatment chamber or a treatment carrier for the medical or dental instrument according to claim 14.

23. A treatment chamber or treatment carrier for use in a device for treating a medical or dental instrument, comprising:
- a housing which at least partially surrounds the medical or dental instrument,
- at least one conductor made of an electrically conductive material layer applied to a surface of the housing for converting electrical energy into thermal energy, and
- at least two electrical contacts connected to the conductor to supply electrical energy to the at least one conductor, wherein
- the housing comprises at least one first housing part and at least one second housing part, which are connected so that the first and second housing parts can be rotated or displaced relative to one another for introducing and removing the medical or dental instrument.

24. The treatment chamber or treatment carrier according to claim 23, further comprising at least one of a dielectric carrier layer and a dielectric cover layer to electrically insulate the conductor.

25. The treatment chamber or treatment carrier according to claim 24, wherein at least one of the dielectric carrier layer and the dielectric cover layer is formed by a thick-film or a thin-film coating.

26. The treatment chamber or treatment carrier according to claim 24, wherein the dielectric carrier layer is arranged on one of an inside or outside of the housing, the at least one conductor is arranged on the dielectric carrier layer and the dielectric cover layer is arranged on the at least one conductor.

27. The treatment chamber or treatment carrier according to claim 23, wherein the at least one conductor is arranged on at least one of an inside and an outside of the housing.

28. The treatment chamber or treatment carrier according to claim 23, wherein the at least one conductor is arranged on the housing to surround the at least one medical or dental instrument on at least two sides.

29. The treatment chamber or treatment carrier according to claim 23, wherein the at least one conductor is a first conductor, further comprising at least a second conductor, and wherein the first conductor and the second conductor can be separately supplied with electrical energy.

30. The treatment chamber or treatment carrier according to claim 23, wherein the at least one conductor is formed by a thick-film or a thin-film coating.

31. The treatment chamber or treatment carrier according to claim 23, wherein the housing comprises at least one of: a connecting device for connecting the instrument to the treatment chamber or treatment carrier and a media feed for introducing at east one operating medium into the treatment chamber or into the treatment carrier.

32. A device for treating a medical or dental instrument, comprising:

a control unit for controlling and/or regulating a treatment process, a power supply for connecting the treatment device to a power source, at least one media supply having at least one of a media storage device and a connection for an external media source, and a treatment chamber or a treatment carrier for the medical or dental instrument according to claim 23.

* * * * *